(12) United States Patent
Hoernig et al.

(10) Patent No.: US 8,605,854 B2
(45) Date of Patent: Dec. 10, 2013

(54) MAMMOGRAPHY APPARATUS WITH X-RAY SOURCES ARRANGED AT DIFFERENT DISTANCES FROM THE CHEST

(75) Inventors: Mathias Hoernig, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 71 days.

(21) Appl. No.: 13/178,897

(22) Filed: Jul. 8, 2011

(65) Prior Publication Data

US 2012/0008739 A1    Jan. 12, 2012

(30) Foreign Application Priority Data

Jul. 8, 2010   (DE) .................. 10 2010 026 434

(51) Int. Cl.
*A61B 6/00*   (2006.01)
(52) U.S. Cl.
USPC ................................................ 378/37; 378/9
(58) Field of Classification Search
USPC ........................................ 378/37, 9
See application file for complete search history.

(56) References Cited

U.S. PATENT DOCUMENTS

| 6,901,132 | B2 | 5/2005 | Eberhard et al. | |
|---|---|---|---|---|
| 7,945,014 | B2 | 5/2011 | Mertelmeier | |
| 7,965,812 | B2 | 6/2011 | Hanke et al. | |
| 2009/0310844 | A1 | 12/2009 | Ludwig et al. | |
| 2009/0323893 | A1* | 12/2009 | Hanke et al. | 378/37 |
| 2010/0034450 | A1 | 2/2010 | Mertelmeier | |
| 2010/0246759 | A1* | 9/2010 | Ogura et al. | 378/21 |
| 2011/0122992 | A1* | 5/2011 | Hanke et al. | 378/37 |

FOREIGN PATENT DOCUMENTS

DE        10 2008 033 150 A1    2/2010

* cited by examiner

*Primary Examiner* — Hoon Song
(74) *Attorney, Agent, or Firm* — Schiff Hardin LLP

(57) ABSTRACT

A mammography apparatus has at least one x-ray source to emit x-ray radiation and an x-ray detector with a number of pixels. The mammography apparatus is designed so that the x-ray radiation is emitted into the breast tissue of a patient at a number of positions, and the x-ray radiation is detected by the x-ray detector after it passed through the breast tissue. The positions have different distances from the shoulder-to-shoulder axis of the patient.

12 Claims, 5 Drawing Sheets

MAMMOGRAPHY APPARATUS WITH X-RAY SOURCES ARRANGED AT DIFFERENT DISTANCES FROM THE CHEST

BACKGROUND OF THE INVENTION

1. Field of the Invention

The present invention concerns a mammography apparatus in which x-ray sources have different distances from the chest.

2. Description of the Prior Art

In a tomosynthesis procedure, a three-dimensional image is generated from a number of two-dimensional images. A two-dimensional image or a projection of the tissue to be examined that the x-ray beam passes through is generated by an x-ray device with an x-ray source and a detector. The two-dimensional image depicts the attenuation of the tissue in the volume that the beam has passed through. A second two-dimensional image or a second projection of the same tissue or volume is acquired after the radiation source and/or the detector has been moved into a second position. A three-dimensional tomosynthesis image can be generated by a computerized reconstruction after a number of such two-dimensional images have been acquired.

One field of application of the aforementioned three-dimensional imaging method is mammography. An image generation device that is typically used in mammography has a pivotable x-ray source and a stationary x-ray detector. The tissue to be examined is positioned over the stationary detector. The x-ray source is subsequently pivoted in multiple steps, for example in a range of +/−25°, and a number of two-dimensional x-ray images is acquired from different pivot positions of the x-ray source with the stationary detector. Naturally, it is also possible to use a number of stationary x-ray sources or to displace the x-ray source only in a translational manner. The detector can also be shifted or pivoted counter to the movement of the x-ray source. The x-ray source(s) emits or emit x-rays from positions that are arranged along a line that runs parallel to the shoulder-to-shoulder axis of a patient. By using a beam path parallel to the chest wall, the entire tissue of the breast is imaged and the chest is not exposed to radiation. A three-dimensional image is generated from the multiple two-dimensional x-ray images by means of the reconstruction. Imaging methods and devices for the mammography of this type are described in DE 10 2006 046 741 A1, DE 10 2008 004 473 A1, DE 10 2008 033 150 A1, EP 2 138 098 A1 and DE 10 2008 028 387 A1, for example.

Filtered back projection techniques (that are described Imaging Systems for Medical Diagnostics, Arnulf Oppelt, Publicis Corporate Publishing, Erlangen, ISBN 3-89578-226-2, Chapter 10.5, for example) are known for use for the reconstruction of a three-dimensional image from a plurality of two-dimensional images. These filtered back projection methods present reconstructed images with a high contrast and a high accuracy of detail but lose information about the relative tissue density due to the missing data given tomosynthesis with limited scan angle.

The breast is composed primarily of glandular tissue, fat tissue, connective tissue and blood vessels. The x-ray attenuation coefficients of these tissue types are very similar, which significantly hinders the evaluation of three-dimensional mammography images. The primary field of application of imaging methods in mammography is the early detection of cancerous tissue. It is additionally made more difficult in that cancerous tissue has an x-ray attenuation coefficient similar to other tissue types. Mammography methods are described in Imaging Systems for Medical Diagnostics, Arnulf Oppelt, Chapter 12.6, Publicis Corporate Publishing, Erlangen, ISBN 3-89578-226-2, for example.

As mentioned above, in the prior art an x-ray source is moved, or x-ray sources are moved along a line that runs parallel to the shoulder-to-shoulder axis of the patient. The linear scanning over a limited angle range leads to a limited depth resolution. Therefore, conventional mammography apparatuses and mammography methods have a limited sensitivity and specificity.

SUMMARY OF THE INVENTION

An object of the present invention is to provide a mammography apparatus and a mammography method that have a higher depth resolution.

This object is achieved in accordance with the invention by a mammography apparatus with at least one x-ray source that emits x-ray radiation and an x-ray detector with a number of pixels, wherein the x-ray radiation is emitted at a number of positions in the breast tissue of a patient and the x-ray radiation is detected by the x-ray detector after it has passed through the breast tissue. According to the invention, the positions at which the x-ray radiation is emitted respectively have different distances from the shoulder-to-shoulder axis of the patient.

The mammography apparatus can make use of an x-ray tube of the type known as a multifocus x-ray tube. A multifocus x-ray tube has a number of x-ray sources that are activated in succession. The x-ray sources can make use of carbon nanotubes. The multifocus x-ray source can have conventional, individually controllable cathodes, for example dispenser cathodes. The multifocus x-ray source can have individually controllable cold cathodes, for example field emitters. A suitable x-ray source is described in the aforementioned EP 2 138 098 A1, DE 10 2008 033 150 A1 and DE 10 2008 004 473 A1, for example.

The multiple x-ray emitters are arranged parallel to the shoulder-to-shoulder axis of the patient in front of the chest. The multiple x-ray sources of each emitter are arranged so that the entire breast tissue of a patient is detected during an examination but the chest is not exposed. The x-ray radiation emitted by the x-ray sources is detected by the detector after it has passed through the breast tissue. These x-ray sources that are arranged parallel to the shoulder-to-shoulder axis of the patient have a first distance from the shoulder-to-shoulder axis of the patient.

At least one x-ray source is arranged at a position that has a second distance from the shoulder-to-shoulder axis of the patient. The second distance is greater than the first distance. X-ray radiation is thereby emitted from a different distance, passes through the breast tissue of the patient and strikes the x-ray detector. A number of x-ray detectors can be arranged with different distances from the shoulder-to-shoulder axis of the patient.

Such a mammography apparatus has the advantage that slice exposures from an additional plane are created for the image reconstruction and volume reconstruction. The three-dimensional reconstruction receives more spatial information. The image reconstruction receives additional data from a plane that is located 90° relative to the chest wall. When a number of x-ray sources or an x-ray source with a number of x-ray positions emitting x-ray radiation are used, additional information is acquired without mechanical movement during a scan in which the x-ray sources are activated in succession and/or x-ray radiation is emitted in succession at different positions of the x-ray source. However, it is also possible to use one or more movable x-ray sources. The positions at which the x-ray radiation is emitted can be located on a horizontal plane across the breast of the patient. The positions can be arranged in a circle, rectangle or square across the breast of the patient. A circular tomosynthesis can thereby be applied. A higher depth resolution and an isotropic resolution of the image plane can be achieved in the circular tomosynthesis. Moreover, the diagnostic data acquisition can take place three-dimensionally, and tissue samples can be examined three-dimensionally.

A number of positions at which x-ray radiation is emitted can be arranged in a line parallel to the shoulder-to-shoulder axis, and a number of positions can be arranged on a line perpendicular to the shoulder-to-shoulder axis. The positions at which x-ray radiation is emitted can be arranged in a T-shape, U-shape or π-shape. A range of angles from −25° to +25° thus can be achieved in a direction that is parallel to the shoulder-to-shoulder axis of the patient. Moreover, a range of angles from 0 to 15° can be achieved in a direction that is orthogonal to the shoulder-to-shoulder axis of the patient. If a T-shaped arrangement of positions emitting the x-ray radiation is used, the x-ray sources arranged orthogonal to the shoulder-to-shoulder axis of the patient are essentially located over the middle of the breast.

At least 15 positions emitting x-ray radiation can be arranged in the T-shaped arrangement, parallel to the shoulder-to-shoulder axis of the patient, and at least three positions emitting x-ray radiation can be arranged perpendicular to the shoulder-to-shoulder axis of the patient. One scan trajectory is thus provided parallel to the shoulder-to-shoulder axis of the patient, and one scan trajectory is provided perpendicular to the shoulder-to-shoulder axis of the patient.

If a U-shaped or π-shaped arrangement of positions emitting x-ray radiation is used, the positions are advantageously arranged in lines next to the breast to the right and left, wherein these lines are aligned so that they are located perpendicular to the shoulder-to-shoulder axis of the patient. A scan trajectory is thus provided that runs parallel to the shoulder-to-shoulder axis of the patient. Two scan trajectories are also provided that run perpendicular to the shoulder-to-shoulder axis of the patient.

The positions emitting the x-ray radiation can be arranged like a matrix. Arbitrary scan trajectories thus can be achieved that can run parallel, orthogonal or at an angle to the shoulder-to-shoulder axis of the patient. The scan trajectories can be freely programmable.

At a position emitting an x-ray beam that is further removed from the shoulder-to-shoulder axis than those positions that are located nearest to the shoulder-to-shoulder axis, the x-ray radiation can be emitted at an angle relative to vertical in the direction of the breast tissue. The intensity of the x-ray beam striking the x-ray detector thus can achieve a relatively high value without the breast tissue being exposed with a high radiation dose.

The x-ray source can be a multifocus x-ray tube and/or a microfocus x-ray tube. The x-ray source can generate the x-ray radiation both by means of conventional emitter technology (i.e. thermal emission—and by means of cold emission (i.e. field emitters). The cold emission and the field emitter can be realized by what are known as carbon nanotube emitters, for example. The x-ray source can have only one cathode and one anode, wherein a beam deflection unit has the effect that the x-ray beam is emitted from the desired position. It is also possible to use an x-ray source with one cathode and a plurality of anodes. The x-ray source can have at least one collimator that has the effect that the x-ray radiation passes only through the tissue to be examined and not through other tissue.

The number of positions at which an x-ray beam can be emitted for an acquisition can correspond to the number of pixels of the x-ray detector. This has the advantage that an image reconstruction is required for a projection image.

The invention also encompasses a mammography method with the following steps: emit x-ray radiation into the breast tissue at least one first position and emit x-ray radiation into the breast tissue at least one second position that is located further removed from the shoulder-to-shoulder axis of the patient than the at least one first position. A number of first and second positions can be used. The first positions can be arranged along a line that runs parallel to the shoulder-to-shoulder axis of the patient.

The first and second positions can be arranged in a T-shape, U-shape, π-shape, in the form of a matrix, in the form of a circle, in the form of a square or in the form of a rectangle.

The present invention also encompasses a non-transitory, computer-readable storage medium that is loadable into a computerized control and processing system of a mammography apparatus, the storage medium being encoded with programming instructions that cause the mammography apparatus to operate in accordance with the present invention as described above, including all embodiments.

DESCRIPTION OF THE PREFERRED EMBODIMENTS

Figure 9:
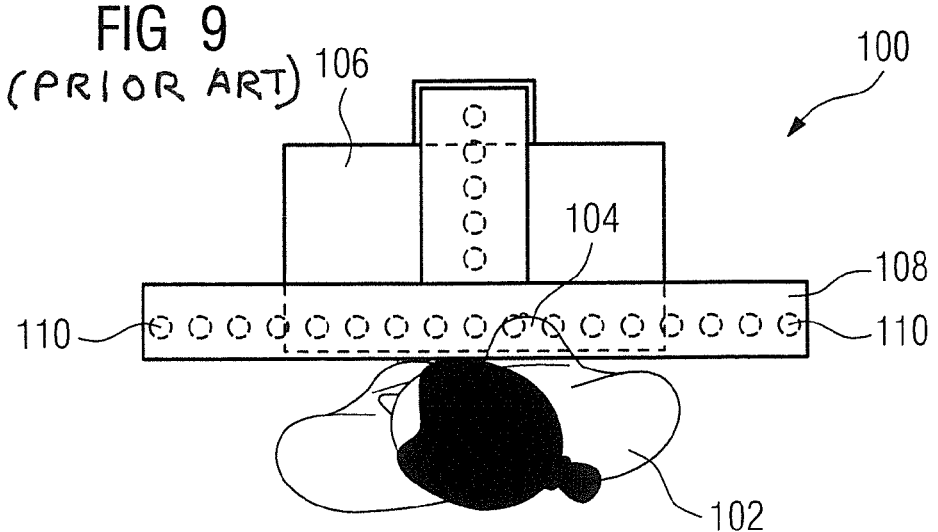
FIG. 9 is a partially cut-away plan view of a mammography apparatus of the prior art.
Figure 10:
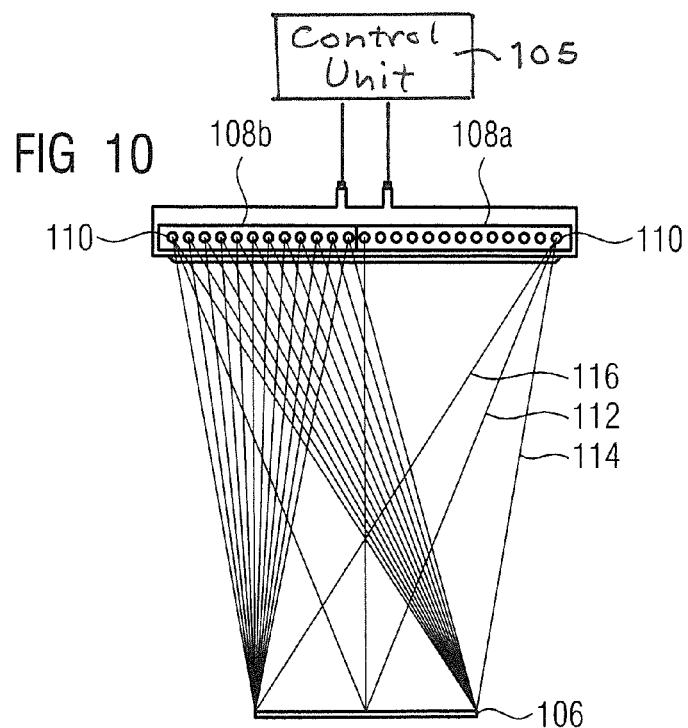
FIG. 10 shows a detail of a mammography apparatus of the prior art.
Figure 11:
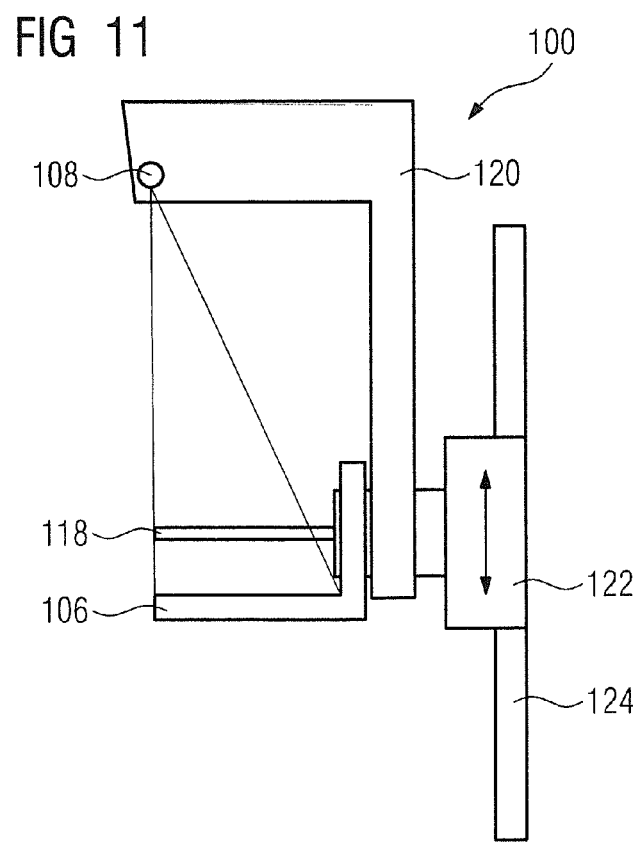
FIG. 11 is a partially cut-away side view of a mammography apparatus of the prior art.

FIG. 9 shows a partially cut-away plan view of a mammography apparatus 100 of the prior art; FIG. 10 shows a multifocus x-ray tube arrangement of the prior art; and FIG. 11 shows a partially cut-away side view of a mammography apparatus of the prior art. A patient 102 whose breast 104 should be examined by the mammography apparatus 100 places her breast on an x-ray detector 106. The breast is compressed by a compression plate for x-raying. The conventional mammography apparatus has a mount 120 that is arranged so as to be moved by a guide 122 on a stand 124 so that the detector 106 and the compression plate 112 can be moved to the desired height. The compression plate 118 is arranged so as to be movable relative to the detector 106. The mammography apparatus 100 has at least one multifocus x-ray tube 108 in which a number of beam-emitting positions 110 are located. The beam-emitting positions 110 can be x-ray sources that, for example, are made from a carbon nanotube material. The positions emitting x-ray radiation can also be individually controllable thermal cathodes, for example dispenser cathodes.

FIG. 10 shows an example in which two multifocus x-ray tubes 108*a* and 108*b* are present that respectively have a number of positions 110 emitting x-ray beams.

The positions 110 from which x-ray beams are emitted are activated in succession by a control unit 105 so that a scan trajectory in one direction parallel to the shoulder-to-shoulder axis of the patient 102 is formed along which an x-ray beam is successively emitted from different positions 110.

The position 110 emitting an x-ray beam emits a central ray 112, a right boundary ray 114 and a left boundary ray 116. In order to protect the patient from an unnecessary radiation exposure, the position 110 emitting an x-ray beam outputs no x-ray radiation outside of the right boundary ray 114 and the left boundary ray 116. The aperture angle of the x-ray radiation can be limited by collimators (not shown). The right boundary ray 114 strikes the right end of the detector 106, the left boundary ray 116 strikes the left end of the detector 106 and the central ray 112 strikes the middle of the detector 106. Additional positions 110 emitting an x-ray radiation successively emit an x-ray beam, such that the breast tissue is traversed by x-ray radiation from different angles. This x-ray radiation strikes the detector 106, which advantageously is a solid-state detector. Via the detector 106, a projection exposure is generated by each beam that is emitted by a position 110. The number of projection exposures is stored in a computer memory (not shown), and the three-dimensional volume from which two-dimensional slice views can be created is reconstructed via the algorithms described above.

In the example from the prior art that is shown in FIG. 11, an x-ray source 108 can be provided with only one position emitting an x-ray beam. The mount 120 is arranged such that it can be pivoted relative to the guide 122, such that the mount 120 and the x-ray source 108 can be pivoted on an axis perpendicular to the plane of the thorax.

Figure 1:
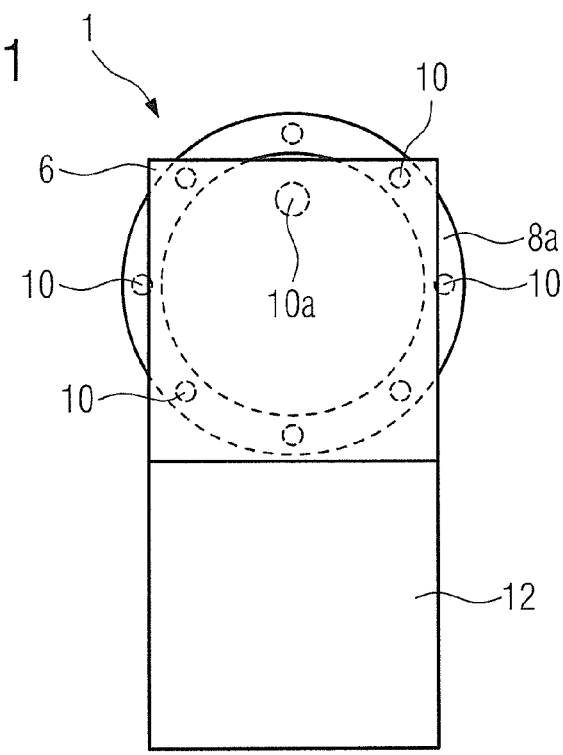
FIG. 1 shows a first embodiment of the invention in which the positions emitting an x-ray beam are arranged in the shape of a circle.

FIG. 1 shows a partially cut-away plan view of a mammography apparatus 1 according to the invention. The mammography apparatus has an x-ray source 8*a* with a number of positions 10 that emit an x-ray beam and are arranged in the shape of a circle. The x-ray beam propagates from the positions 10 through the breast tissue (not shown) and strikes the detector 6 with an optional enlargement table. An additional x-ray radiator—for example a conventional x-ray radiator—is located as a position 10*a* emitting an x-ray beam in the circular arrangement of positions 10 emitting x-rays.

Figure 2:
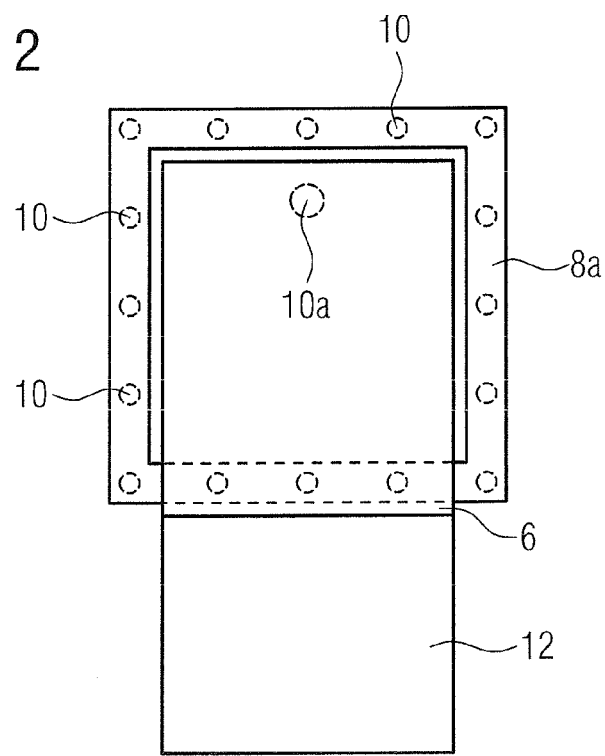
FIG. 2 shows a second embodiment of the invention in which the positions emitting an x-ray beam are arranged in a square.

FIG. 2 is a second embodiment that resembles the first embodiment, wherein the x-ray source 8*b* has positions 10, arranged in a square, that emit an x-ray beam. As in the embodiment of FIG. 1, the x-ray beam travels from the positions 10 through the breast tissue (not shown) and strikes the detector 6 with an optional magnification table. An additional x-ray radiator—for example a conventional x-ray radiator—is located as a position 10*a* emitting an x-ray beam in the quadratic arrangement of positions 10 emitting x-rays.

The slice images acquired by the detector 106 can be processed by means of circular tomosynthesis. This has the advantage that the diagnostic clarification can take place three-dimensionally, and tissue samples can be examined three-dimensionally. Moreover, circular tomosynthesis offers a higher depth resolution and an isotropic resolution in the image plane. The angle range generated by the number of positions 10 emitting x-ray radiation can be −7.5° to +7.5°, preferably +25° to −25°.

Figure 3:
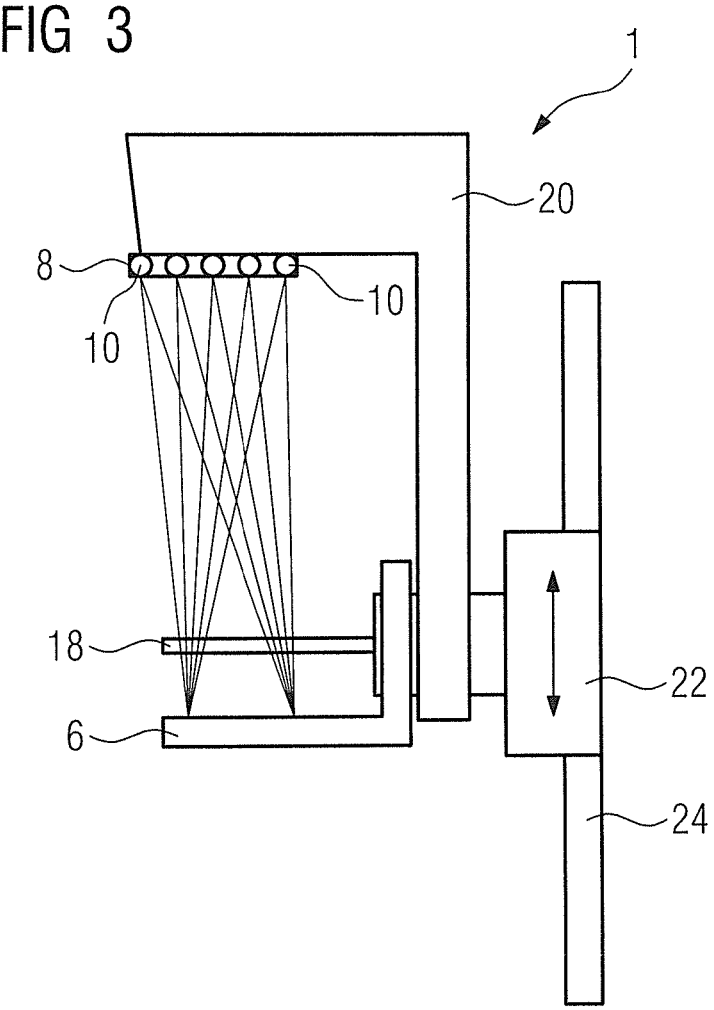
FIG. 3 is a partially cut-away side view of a tomography apparatus according to the invention.

FIG. 3 shows a partially cut-away side view of a mammography apparatus 1 according to the invention. A stand 24 holds a mount 22 via a guide 22, at which mount 20 the multifocus x-ray tube 8 is attached with a plurality of positions 10 emitting an x-ray beam. The multifocus x-ray tube 8 can be a circular multifocus x-ray tube 8*a* or a quadratic multifocus x-ray tube 8*c*. As described in detail in the following, the multifocus x-ray tube 8 can be fashioned in a T-shape, U-shape, π-shape or in the form of a matrix. The detector 6 with the optional magnification table is attached at the mount 12. The detector can be selectively read out in the active field of view. The detector can advantageously be read out quickly. A movable compression plate 18 is arranged on the mount 20. The x-ray beams travel successively from the positions 10 emitting an x-ray beam through the breast of the patient to the detector.

In this embodiment the entire arrangement—i.e. what is known as the "gantry"—that includes the x-ray source and the x-ray detector can be pivoted, for example in order to acquire CC projections (from below), MLO projections (from above) or also ML projections (from the side).

Figure 4:
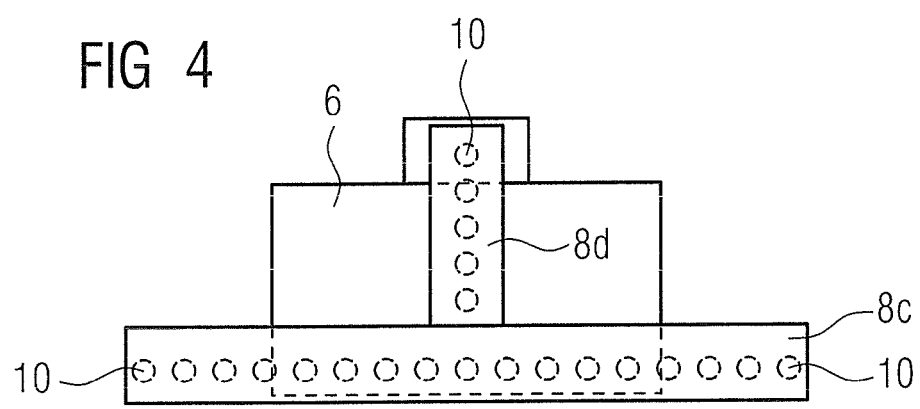
FIG. 4 is a partially cut-away plan view of a third embodiment of the present invention in which the positions emitting an x-ray beam are arranged in a T-shape.

FIG. 4 shows a third embodiment of the invention in which the positions 10 emitting an x-ray beam are arranged in a T-shape. The third embodiment has a first multifocus x-ray tube 8*c* whose positions 10 emitting an x-ray beam are arranged along a line that runs parallel to the axis from shoulder to shoulder of a patient. An angle spectrum from −25° to +25° can be achieved by the first multifocus x-ray tube 8*x*. The third embodiment additionally has a second multifocus x-ray tube 8*d* whose positions 10 emitting an x-ray beam are arranged orthogonal to the shoulder-to-shoulder axis of a patient. An angle spectrum from approximately 0 to 15° (advantageously 0 to 25°) in a direction orthogonal to the chest wall can be achieved via the beam-emitting positions 10. The first multifocus x-ray tube 8*c* generates a first scan trajectory that is arranged parallel to the axis running from shoulder to shoulder of a patient. The second multifocus x-ray tube 8*d* generates a second scan trajectory that is arranged orthogonal to the shoulder-to-shoulder axis of a patient. The x-ray beams strike the detector 6 after they have passed through the tissue.

Twenty-two stationary positions 10 emitting an x-ray beam are advantageously provided. A first position 10 is located at the intersection point of the lines of the T-shape. At least eight positions emitting an x-ray beam are respectively arranged to the right and left of the position at the intersection point of the lines of the T-shape, parallel to the shoulder-to-shoulder axis of a patient. At least five positions 10 emitting an x-ray beam are arranged in the line orthogonal to the shoulder-to-shoulder axis of the patient.

Figure 5:
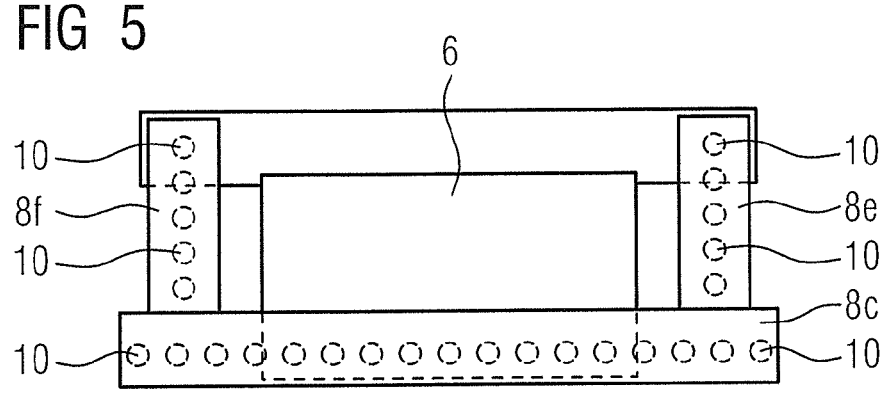
FIG. 5 is a partially cut-away plan view of the fourth embodiment of the invention in which the positions emitting an x-ray beam are arranged in a π-shape.

FIG. 5 shows a fourth embodiment of the invention. The fourth embodiment essentially corresponds to the third embodiment except that two multifocus x-ray tubes 8*e*, 8*f* are present, whose positions 10 emitting an x-ray beam are respectively arranged on a line that are arranged orthogonal to the shoulder-to-shoulder axis of a patient.

The fourth embodiment thus has three scan trajectories. The first scan trajectory runs parallel to the shoulder-to-shoulder axis of a patient. The second and third scan trajectory respectively runs orthogonal to the shoulder-to-shoulder axis of the patient. The right multifocus x-ray tube 8*e* and the left multifocus x-ray tube 8*f* can be arranged so as to be movable, such that they can be shifted into a position in which optimal acquisition conditions are to be expected. The x-ray beams strike the detector 6 after they have passed through the tissue.

Figure 6:
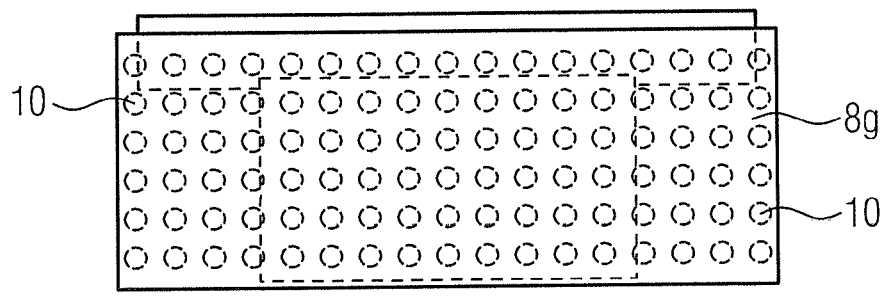
FIG. 6 is a partially cut-away plan view of a fifth embodiment of the invention in which positions emitting the x-ray beam are arranged like a matrix.

FIG. 6 shows the fifth embodiment of the invention in which a multifocus matrix x-ray tube 8g is provided. The positions 10 emitting an x-ray beam are arranged in a matrix on the multifocus matrix x-ray tube. A number of scan trajectories are thereby possible that run parallel to the shoulder-to-shoulder axis of a patient. A number of scan trajectories are also possible that run orthogonal to the shoulder-to-shoulder axis of a patient. Moreover, scan trajectories are possible that run at an angle to the shoulder-to-shoulder axis of the patient. The x-ray beams strike the detector 6 after they have passed through the tissue.

Figure 7:
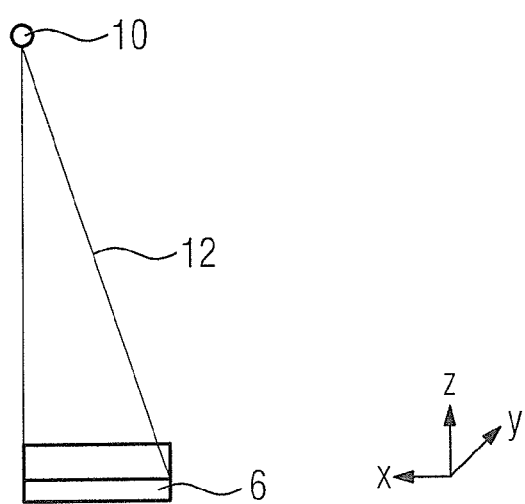
FIG. 7 shows a side view of a typical x-ray course.

FIG. 7 shows a side view of a position 10 emitting an x-ray beam, the position 10 being located in the second multifocus x-ray tube 8d, the third multifocus x-ray tube 8e, the fourth multifocus x-ray tube 8f or in the multifocus matrix x-ray tube 8g at a position that is further removed from the shoulder-to-shoulder axis of the patient than another position emitting an x-ray beam. The x-ray beam emitted from this position 10 travels through the breast tissue to the detector at an angle of 0 to 15° (advantageously 0° to 20°) relative to the vertical axis. The beam must be limited so that it does not enter into the chest of the patient.

Figure 8:
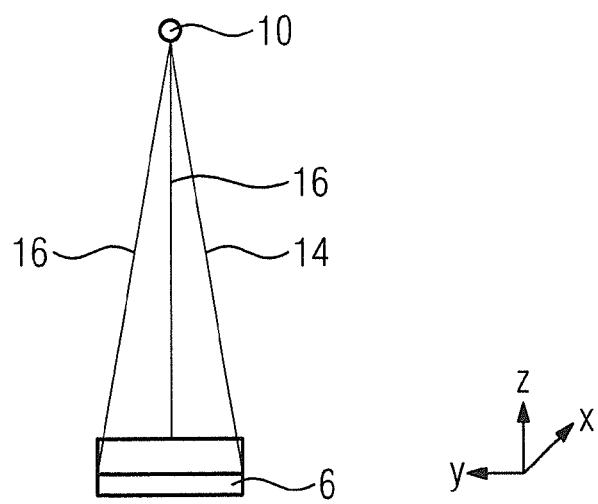
FIG. 8 shows a frontal view of a typical x-ray course.

FIG. 8 shows a frontal view of a position 10 emitting an x-ray radiation. The x-ray radiation emits [sic] a central ray 12 as well as a right boundary ray 14 and a left boundary ray 16. X-ray radiation that travels through the breast and strikes the detector is likewise emitted between the right boundary ray and the left boundary ray. The right boundary ray 14 thereby strikes the right edge of the detector 6, the central ray strike the middle of the detector 6 and the left boundary ray 16 strikes the left edge of the detector 6.

Each of the positions 10 emitting an x-ray radiation can have an x-ray source with a collimator.

The x-ray foci—i.e. the optical focal spots—in mammography are typically smaller than 1 mm×1 mm. The nominal value is approximately 0.3 mm to approximately 0.4 mm and, in magnification mammography, is approximately 0.1 mm to approximately 0.2 mm. The aforementioned embodiments have approximately 10 to approximately 100 or even more positions emitting x-ray radiation. The angle range within which an x-ray beam is generated is typically between approximately 10° and approximately 60°. The distance between the x-ray source and the x-ray detector at the central ray is normally approximately 500 mm to approximately 700 mm, advantageously approximately 660 mm.

The present invention has the advantage that slice exposures from an additional plane are provided for the image reconstruction and volume reconstruction. Flexible, asymmetrical scan trajectories from at least two directions orthogonal to one another are possible. More spatial information is provided for three-dimensional image reconstruction. The additional information can be acquired during the scan without mechanical movement. Data from a plane at 90° relative to the chest wall are provided for the image reconstruction. Flexible scan trajectories that can be defined depending on the clinical question are possible given a multifocus matrix x-ray tube. If multifocus x-ray tubes or multifocus matrix x-ray tubes are used, no movement artifacts arise since the scans are implemented without mechanical movements.

The invention encompasses an examination method and a mammography apparatus for auxiliary acquisitions for diagnostic clarification, for a magnification exposure, for a biopsy direction and a tissue sample examination with a circular tomosynthesis by means of a tube, a generator, a detector, an acquisition workstation (PC) to control the acquisition and display the images, and for image reconstruction. In addition to the conventional x-ray tube as a primary radiator, the mammography apparatus has, as a primary radiator, a multifocus tube with x-ray emitters that are arranged in a circle or in a rectangle around the primary radiator. Radiation collimators are provided that ensure for each x-ray source that only at most the surface of the detector is irradiated. An indicator of the usable field of view at the detector is provided in which the subject to be examined should be centered. The multifocus sources can be individually controllable cold cathodes (field emitters), wherein the cathodes are made up of carbon nanotube (CNT) material. As an alternative, the multifocus sources can be conventional, individually controllable thermal cathodes (dispenser cathodes, for example). The detector can be a solid-state detector that can be read out quickly. The detector can selectively be read out in the active field of view. A magnification table can optionally be used.

The present invention is based on the insight that circular tomosynthesis can be applied to breast applications with a small field of view. The advantages are that the diagnostic clarification can take place three-dimensionally, tissue samples can be examined three-dimensionally, a higher depth resolution can be achieved and the isotropic resolution in the image plane can be improved.

The mammography apparatus can have a computer system in whose memory are stored the projection images acquired by the detector. The computer can have a control program that successively activates the positions 10 emitting an x-ray beam in the desired order. The computer system can also have an evaluation software that generates a three-dimensional representation of the tissue from the projection images. The three-dimensional representation can be presented on a monitor (not shown), for example in the form of slice images.

It is understood that the invention can also be applied in other medical fields. For example, the invention can be used to x-ray the abdomen, the head, a joint area or any other body region.

Although modifications and changes may be suggested by those skilled in the art, it is the intention of the inventor to embody within the patent warranted hereon all changes and modifications as reasonably and properly come within the scope of his contribution to the art.

We claim as our invention:

1. A mammography apparatus comprising:
   an x-ray source that emits x-ray radiation;
   an x-ray detector comprised of a plurality of detector pixels;
   said x-ray source and said x-ray detector being mounted with said x-ray source at a stationary position relative to said x-ray detector, and said x-ray source being adapted to irradiate breast tissue of a patient, located between said x-ray source and said x-ray detector, with said x-ray radiation, said x-ray radiation being detected by said x-ray detector after passing through said breast tissue;
   said x-ray source being configured to emit said x-ray radiation from each of a plurality of different emission-originating positions within said x-ray source that are located at respectively different distances from a frontal plane of the patient that is parallel to a shoulder-to-shoulder axis of the patient so as to irradiate said breast tissue from a plurality of different directions;

said plurality of different emission-originating positions being arranged in a geometrical shape selected from the group consisting of a T-shape, a U-shape, and a π-shape; and a control unit configured to operate said x-ray source to cause x-ray radiation to be emitted respectively at said different positions in succession.

2. A mammography apparatus as claimed in claim 1 wherein said x-ray source is configured to irradiate said breast tissue at said different positions along a horizontal plane over a breast of the patient containing said breast tissue.

3. A mammography apparatus as claimed in claim 1 wherein said x-ray source is configured to irradiate said breast tissue with said x-ray radiation from said plurality of positions along a line parallel to said shoulder-to-shoulder axis of the patient and along a line perpendicular to the shoulder-to-shoulder axis of the patient.

4. A mammography apparatus as claimed in claim 1 wherein said x-ray source is configured to irradiate said breast tissue from said plurality of positions arranged in a matrix formation.

5. A mammography apparatus as claimed in claim 1 wherein said plurality of positions include a position farthest from the shoulder-to-shoulder axis of the patient and a position located nearest to the shoulder-to-shoulder axis of the patient, and wherein said x-ray source is configured to irradiate said breast tissue with said x-ray radiation between said nearest position and farthest position at an angle relative to vertical in a direction of the breast tissue.

6. A mammography apparatus as claimed in claim 1 wherein said x-ray source is a multifocus x-ray tube comprising a plurality of foci respectively located at said different distances.

7. A mammography apparatus as claimed in claim 6 comprising an electron source formed by carbon nanotubes.

8. A mammography apparatus as claimed in claim 6 wherein said x-ray source comprises a plurality of thermal emitters.

9. A mammography apparatus as claimed in claim 1 wherein said plurality of positions at which said x-ray radiation is emitted corresponds to said plurality of pixels of said x-ray detector.

10. A mammography method comprising the steps of:
stationarily mounting an x-ray source relative to an x-ray detector;
emitting x-ray radiation into breast tissue of a patient from at least one first position in said x-ray source at which said x-ray radiation originates;
emitting x-ray radiation into said breast tissue also from at least one second position in said x-ray source at which said x-ray radiation originates, in succession after emitting said x-ray radiation into breast tissue from said at least one first position, and locating said at least one second position at a distance from a frontal plane of the patient that is parallel to a shoulder-to-shoulder axis of the patient that is father than a distance of said at least one first position from the frontal plane, so as to irradiate said breast tissue from a plurality of different directions;
arranging said plurality of different emission-originating positions in a geometrical arrangement selected from the group consisting of a T-shape, a U-shape, and a π-shape; and
with said x-ray detector, detecting the x-ray radiation passing through the breast tissue originating from each of said at least one first position and said at least one second position.

11. A mammography method as claimed in claim 10 comprising arranging said first position and said second position in a configuration selected from the group consisting of a T-shape, a U-shape, a π-shape, a matrix, a circle, a square, and a rectangle.

12. A non-transitory computer-readable storage medium encoded with programming instructions, said storage medium being loaded into a computerized control and processing system of a mammography apparatus comprising an x-ray source that is stationarily mounted with respect to an x-ray detector, and said programming instructions causing said computerized control and processing system to:
operate said x-ray source to irradiate breast tissue of a patient with x-rays originating from at least one first position in said x-ray source;
operate said x-ray source to also irradiate said breast tissue with x-ray radiation originating from at least one second position in said x-ray source that is father from a frontal plane of the patient that is parallel to a shoulder-to-shoulder axis of the patient than said at least one first position so as to irradiate said breast tissue from a plurality of different directions;
operate said x-ray source to emit x-rays that originate in succession from said at least one position and said at least one second position in a geometrical arrangement selected from the group consisting of T-shapes, U-Shapes and π-shapes; and
operate said radiation detector to detect x-rays passing through the breast tissue from said at least one first position and said at least one second position.

* * * * *